(12) United States Patent
Lang et al.

(10) Patent No.: US 10,527,563 B2
(45) Date of Patent: Jan. 7, 2020

(54) ANALYSIS WITH PRELIMINARY SURVEY

(71) Applicant: OXFORD INSTRUMENTS NANOTECHNOLOGY TOOLS LIMITED, Oxon (GB)

(72) Inventors: Christian Lang, Oxon (GB); James Corrin, Oxon (GB)

(73) Assignee: OXFORD INSTRUMENTS NANOTECHNOLOGY TOOLS LIMITED, Oxon (GB)

( * ) Notice: Subject to any disclaimer, the term of this patent is extended or adjusted under 35 U.S.C. 154(b) by 0 days.

(21) Appl. No.: 16/099,638

(22) PCT Filed: May 9, 2017

(86) PCT No.: PCT/GB2017/051283
§ 371 (c)(1),
(2) Date: Nov. 7, 2018

(87) PCT Pub. No.: WO2017/194925
PCT Pub. Date: Nov. 16, 2017

(65) Prior Publication Data
US 2019/0187079 A1      Jun. 20, 2019

(30) Foreign Application Priority Data

May 9, 2016   (GB) .................................. 1608056.6

(51) Int. Cl.
*G01N 23/00*    (2006.01)
*G01N 23/2252*  (2018.01)
*G06K 9/00*     (2006.01)

(52) U.S. Cl.
CPC ..... *G01N 23/2252* (2013.01); *G06K 9/00127* (2013.01); *G01N 2223/079* (2013.01); *G01N 2223/321* (2013.01); *G01N 2223/401* (2013.01)

(58) Field of Classification Search
CPC ......... G01N 23/2252; G01N 2223/321; G01N 2223/401; G01N 2223/079; G01N 2223/076; G01N 2223/6116; G01N 2223/6462; G06K 9/00127; H01J 2237/221; H01J 2237/24585; H01J 2237/2806; H01J 2237/2807
USPC ................................ 250/306, 307, 310, 311
See application file for complete search history.

(56) References Cited

U.S. PATENT DOCUMENTS

| | | | |
|---|---|---|---|
| 6,476,388 B1* | 11/2002 | Nakagaki | G01N 23/225 250/306 |
| 2005/0121610 A1* | 6/2005 | Abe | G01N 23/2251 250/310 |
| 2013/0126729 A1* | 5/2013 | Own | C12Q 1/6869 250/307 |

* cited by examiner

*Primary Examiner* — Michael Maskell
(74) *Attorney, Agent, or Firm* — Blank Rome LLP

(57) ABSTRACT

A method and apparatus for analysis of a specimen in a microscope are provided. A first survey is performed that collects analytical data from a region of interest on the specimen surface using a first set of conditions. A second survey is performed that collects additional analytical data from selected parts of the region of interest on the specimen surface using a second set of conditions, different from the first set of conditions. The analytical data from the first survey is used to select the parts used for data collection in the second survey and to decide the order in which they are used.

20 Claims, 3 Drawing Sheets

(a)

(b)

(c)

(d)

(e)

(f)

ANALYSIS WITH PRELIMINARY SURVEY

This application is a U.S. national stage application based on International Application No. PCT/GB2017/051283, filed May 9, 2017, which claims priority to Great Britain Patent Application No. 1608056.6, filed May 9, 2016, both of which are herein incorporated by reference in their entirety.

FIELD OF INVENTION

The invention relates to a method and apparatus for analysis of a specimen in a microscope, which in particular improve the speed and sample throughput for analysis of particles on a specimen that involves a combination of fast imaging and slow stage movement to cover a large area on the specimen.

BACKGROUND TO THE INVENTION

When a focussed electron beam strikes a specimen, signals are generated that are representative of the material excited by incident electrons. In a scanning electron microscope, the position of such a focussed electron beam on the specimen surface can be controlled by deflecting the beam using electrostatic or electromagnetic methods. The analysis control system will typically position the beam at a series of points on a grid. At each point one or more signals are measured and the values obtained for each type of signal corresponding to that point are recorded. The values for a signal obtained on a regular rectangular grid form a digital image from a field of view. The electron beam can be deflected very fast but the magnitude of the deflection is limited by the electron optics because there is increasing distortion at large deflection angles. Therefore the field of view may only cover a small area on the specimen surface. If a large area of the specimen surface has to be covered, a new field of view can be brought under the beam by moving the specimen stage that supports the specimen. Thus, by a combination of stage movements and beam deflections, the whole surface of the specimen may be surveyed in a series of fields of view. The components of an example apparatus for automated particle analysis are show in FIG. 1.

The time to scan a grid of points over the surface of a specimen depends on the number of points in the grid and the dwell time at each point. In a scanning electron microscope, electron signals usually have much better signal-to-noise than other analytical signals such as x-ray spectral emissions. This means that useful electron signal information can be obtained with a much shorter dwell per point than for x-ray or other analytical data. It is well known that a fast electron signal scan over the specimen can be used to find out if there are any features (e.g. particles, debris, defects etc.) that make it worthwhile spending additional time for x-ray analysis (e.g. Laskin and Cowin, Anal. Chem. 2001, 73, 1023-1029). This principle is used for finding contaminant particles in precision manufacturing, also called 'technical cleanliness analysis'. Particles are removed from the manufactured part and deposited on a substrate made out of a light element such as carbon. The signal from a backscattered electron detector (BSED) is sensitive to the mean atomic number of the material and if the electron beam strikes a contaminant particle containing heavy elements, the signal will be strong. However, X-ray analysis is still required to determine which elements are present in the particle to identify the source of the contamination. By scanning the electron beam over a grid of points and observing the BSED signal, the location of potentially interesting particles can be found fast without wasting time doing slow x-ray analysis on every point. X-ray analysis time can thus be minimised by concentrating on the most likely particles and the overall search process is efficient.

The electron signal strength mapped over a regular grid of points forms a two dimensional digital image of pixels which take values corresponding to the electron signal at each pixel location. The image can be processed mathematically to identify features such as particles, measure the morphology of individual particles and count the number of particles. If the grid of points is sufficiently fine, then the measurements of particle morphology may be accurate enough to characterise particles without using any additional analytical signal. However, a fine grid means there are more points for the beam to dwell on to get a good electron signal and consequently a longer time to finish a single scan by deflecting the electron beam.

The conventional method of automated particle analysis is exemplified by FIG. 2. FIG. 2(a) shows a specimen where there are a number of particles on the surface. While the stage is stationary, the electron beam is deflected sequentially over a grid of points, typically with a raster scan order, in order to collect a digital image of the electron signal (e.g. backscattered electron signal, BSE) over a small field of view. This is shown schematically in FIG. 2(b). The specimen can be moved in X and Y directions by moving the stage supporting the specimen. Thus the position of the electron beam raster can be arranged to fall on contiguous fields of view that cover a large area on the specimen surface. In FIG. 2(c), 9 contiguous fields are shown labelled in the order in which they will be scanned. FIG. 2(d) shows the particles that will be covered by the raster scans in each field. When field 1 is scanned, the digital image formed using an electron signal (FIG. 2(e)) is processed to find the outlines of individual particles and decide if each particle is of a size and shape to be of interest. For each particle of interest, the electron beam is then either positioned on a point on the particle, or rastered over a grid of points on the particle while x-ray data is acquired (FIG. 2(f)). This is repeated for all the particles to be analysed in field 1. When all particles of interest have been analysed, the specimen stage is moved so that the next field of view can be reached by electron beam scanning. The process is repeated until all 9 fields have been covered.

The region that can be scanned by deflecting an electron beam is limited and a combination of specimen stage movement over a coarse grid and electron beam deflection on a finer grid in between the stage grid points is usually required to scan the whole specimen. The number of points in the electron beam grid and the number of points in the stage grid can be optimised to minimise distortion and deliver "target" data of required accuracy in the fastest possible time. Nevertheless, even if no additional analytical measurements are taken, it may take many stage movements and analysis of many grids of points of electron signal data in order to cover the whole specimen region. If there are no potentially interesting particles found after an electron signal scan, the time for the stage movement and the time to scan the electron beam over that grid of points is essentially wasted. In the worst case, the time for surveying the whole specimen may be wasted and this can be important if there are many specimens to be scanned. The object of the current invention is to improve the productivity for surveying samples.

SUMMARY OF THE INVENTION

In accordance with the invention we provide a method for analysis of a specimen in a microscope, the method comprising:

performing a first survey that collects analytical data from a region of interest on the specimen surface using a first set of conditions;

performing a second survey that collects additional analytical data from selected parts of the region of interest on the specimen surface using a second set of conditions, different from the first set of conditions;

wherein the analytical data from the first survey is used to select the parts used for data collection in the second survey and to decide the order in which they are used.

The inventors have recognised that in many applications of automated particle analysis, more data is collected than is necessary for subsequent decision making. By starting with a first, or preliminary survey, which costs additional time, it is possible to decide on a more optimal strategy for obtaining sufficient target data in the "second" survey so that the total time for preliminary survey and target data acquisition can be much less than the time that would be taken with a regular target data acquisition sequence. The collection of additional analytical data, or "target data acquisition" may use electron beam grid and stage positioning that delivers a required level of accuracy for measuring particle position and morphology and may use sufficient dwell time for electron signal and x-ray signal acquisition to deliver the required level of accuracy of analysis. The first survey, or "preliminary survey", which typically covers the whole area of the specimen, may or may not involve compromising accuracy in order to increase speed to obtain preliminary statistical data for particles on the specimen.

A conventional approach would spend time doing x-ray analysis for particles in every field on a specimen. By using a preliminary survey using electron signals only, for instance, the particle count and particle density is determined for all fields all over the sample very quickly. Statistical data obtained from the preliminary survey scan is then used to optimise the collection of x-ray data so that requirements can be met in the minimum time.

In some embodiments, the analytical information data from the first survey is used to decide the position within the region of interest and order for the selected parts used for data collection in the second survey. Thus the analytical data which may represent the region of interest and may include an indication of the distribution of the features of interest there upon, as monitored or imaged in the first survey can be used in order to optimise the second survey strategy. The parts of the region to be used in the second survey may be selected based upon this distribution. Furthermore, the division of the region into parts, or the decision as to the size, position, or shape of these parts to be scanned in the second survey may be made in accordance with the analytical data, typically including the monitored feature distribution, collected in the first or preliminary survey.

In a typical implementation, it may be necessary to record the position of parts of the region to be used in the second survey, as these "run fields" may not necessarily align, be the same size as, or be contiguous with the survey fields, that is the sub-regions of the region of interest as surveyed in the first survey. The selection of parts for use in the second survey may not necessarily involve obtaining the positions of those parts, but could rather be a decision upon the selection and order of parts whose positions are already determined, or whose positions are not necessarily chosen at this stage.

It is also envisaged that an image of the region of interest may be recorded for the survey area, thus constituting performing the first survey, so that this image can then be processed with a survey scan algorithm so as to perform a feature run, or a second survey, upon it.

In some embodiments, the first set of conditions and data collected during the first survey are chosen so as to give faster coverage of an area on the specimen than for the second set of conditions. In other words, in such embodiments, the conditions of the first survey may be configured such that the rate at which areas of the region of interest are covered is greater for the first survey then for the second survey. An advantage of such an approach would be to further improve the time efficiency of the whole method, while still providing useful information from the first survey that allows the strategy applied to the second survey to be optimised in accordance with the features, or the survey fields containing them, to be prioritised or preferentially covered by the second survey. The additional speed in the first survey may be achieved by compromising or reducing, with respect to the second survey, the precision, accuracy, or resolution of the first survey. For example, the first survey may involve dwelling over each sub-region for a shorter time to produce lower quality images, or it may involve the sub-regions used in the first survey being larger, and thus fewer, than the parts into which the region is subdivided for the second survey.

The conditions of the first and second sets of conditions may comprise any of: magnification, image resolution, image dwell time, a grey level threshold, energy-dispersive x-ray spectroscopy settings, and a survey termination condition. Adjusting these conditions in the first and second survey respectively such that the first set of conditions facilitate the provision of analytical data for use in the second survey, and the second set of conditions results in an optimised strategy for collecting additional, more precise, or more in-depth data on the features of interest, is an advantage provided by such embodiments.

The magnification of the first set of conditions may be lower than the magnification of the second set of conditions, for example. The image resolution of the first set of conditions may be lower than the image resolution of the second set of conditions.

Typically, the first survey comprises collecting the analytical data from the region of interest by moving the specimen with respect to a first detector of the microscope for collecting the analytical data such that each of a plurality of sub-regions is sequentially brought into the field of view of the first detector for a given dwell time. The second survey may comprise collecting the additional analytical data from each of the selected parts by moving the specimen with respect to a second detector of the microscope for collecting additional analytical data such that each of the selected parts is sequentially brought into the field of view of the second detector for a given dwell time. Thus each of the surveys of the method may involve moving a detector with respect to the specimen, or vice versa, such that in each survey the region is imaged or monitored by way of signal collection using a detector, taking pieces of the region in sequence. While the sub-regions of the first survey may typically add up to the entire region of interest, or may be greater in total because of overlaps between the sub-regions, the parts used for the second survey may comprise a subset of the sub-regions used in the first survey, or may comprise all of the sub-regions measured using different conditions, or may comprise parts that are different in size, position, shape, and scanning order from the first survey sub-regions.

In some embodiments the first set and second sets of conditions are chosen such that the number of sub-regions in the first survey is greater than the number of selected parts in the second survey.

In this way the second survey may be performed over a selected few of the parts covered by the first survey. In embodiments where no field overlap is used and the second survey is allowed to proceed to completion, rather than terminating before covering the entire region of interest, then the second survey may include the same number of fields as the first scan.

The first set and second set of conditions may be chosen such that the accuracy of the additional analytical data collected during the second survey is greater than the accuracy of the analytical data collected during the first survey. The first and second sets of conditions applied to the first and second survey respectively may be the same, apart from the additional collection of energy-dispersive x-ray spectroscopy (EDS) data in the second survey. The addition of this information may thus increase the accuracy of the data collected in the second survey.

As noted above, it is possible that the first set and second set of conditions may be chosen such that the image dwell time in the second survey is longer than the dwell time in the first survey. The dwell time can be configured to be sufficiently long to collect the additional analytical data with a predetermined resolution or signal-to-noise ratio. Typically, a specific signal-to-noise ratio may not be set or predetermined for use in the method. However, image resolution and dwell time may be predetermined. The determination of signal-to-noise may, in some embodiments, be made as a qualitative determination by a user or operator.

The first detector may be one and the same as the second detector in some embodiments. Thus the first survey may collect data of the same type, or monitor signals of the same type, as the second survey. Alternatively, the first detector may be separate from the second detector, and may be of a different type. For example, the second detector may have the additional capability of EDS signal collection and as noted above, the collection of additional analytical data in the second survey may comprise collecting energy-dispersive x-ray spectroscopy data.

Typically, using the analytical data from the first survey comprises identifying features of interest on the specimen from the analytical data. Using the analytical data from the first survey may further comprise selecting the parts used for data collection in the second survey such that the selected parts contain a predetermined fraction of the features of interest. In this way, the strategy for performing the second survey may be optimised such that a smaller portion of the region needs to covered by the second survey in order to collect additional analytical data from a predetermined threshold or proportion of the features of interest. Typically, these features of interest are particles or other discrete regions present on a surface of the specimen.

In some embodiments, using the analytical data from the first survey comprises generating an optimal order in which the additional analytical data is collected from each of the selected parts. The order for the second survey, or the path or route with which the second detector is moved with respect to the region may be chosen or generated so that parts of the region containing higher numbers or a higher density of features of interest are covered first, for example. For instance, the detector may front-load the order so that the selected parts for the second survey are scanned in descending order of features of interest contained within each respective part.

The optimal order may thus be generated such that additional analytical data is collected from a part containing a greater proportion of the features of interest before additional analytical data is collected from a part containing a smaller proportion of the features of interest. The total area of the selected parts may be less in some embodiments than the area of the region of interest, and the second survey may comprise collecting the additional analytical data only from the selected parts. Choosing such a limited selection to cover with the second survey may serve to further improve the time efficiency of the method, while minimising the impact upon the quantity or quality of data relevant to features of interest collected in the second survey.

It is envisaged that there may be embodiments wherein the second scan, that is the second survey, is allowed to proceed to completion so as to cover the same area as the first scan, that is the first survey. Whilst this may somewhat negate the point of performing the preliminary, or first, survey, in such embodiments the user or operator may watch or monitor the run or the second survey and may manually terminate the second survey upon deciding that any sufficient portion or area of the region or features of interest there upon have been analysed or had representative data collected therefrom.

Typically, each of the first and second surveys comprises directing a particle beam upon the specimen and detecting the resulting x-rays or electrons emitted from the specimen so as to collect the data. The particle beam may typically be an electron beam or an ion beam.

In some embodiments, the collecting of data in each of the first and second surveys comprises collecting optical image data representing the specimen. For example, an optical image may be taken so that features of interest may be identified or located within the image, so that the second survey can be targeted towards the parts of the region containing those features, for example. In order to further improve efficiency, the first and second sets of conditions can be chosen such that the first survey comprises acquiring optical images having a lower magnification and a smaller field of view than optical images acquired in the second survey. In embodiments involving collecting optical image data in the first and second surveys, the first and second sets of conditions can be chosen such that the first survey comprises acquiring optical images more quickly than optical images acquired in the second survey.

As noted above, using the analytical data from the first survey may comprise identifying features of interest on the specimen from the analytical data. In such embodiments, each of the first and second sets of conditions may include a termination condition in accordance with which each respective survey is terminated, and the termination condition of the second set of conditions may be decided such that the second survey is terminated upon additional analytical data having been collected from a predetermined fraction of the features of interest. The presence of such a termination condition in only the second survey, or the selection of a different termination condition for each of the surveys may constitute the sole difference in conditions for the first and second surveys, or may be one of a plurality of different conditions. Typically, the termination condition will be set later for the first set of conditions than for the second set of conditions, in terms of area coverage of the region of interest.

Depending upon the conditions chosen, it may also be the case that the first survey takes less time than the second survey, as noted above. In some embodiments, the first and second set of conditions may be similar other than the difference in termination condition. In some cases, a user may choose to use the same conditions such as image dwell time, magnification, and resolution, so that it can be reasonably expected that the same number of features will be measured in the first survey as in the second survey. This may be the case when the intention is to use a termination condition to stop the second scan when a specified or predetermined portion of the total numbers of features of interest has been analysed. However, if a field overlap is applied to the second scan, for instance in order to deal with particles situated close to the edges of survey fields, the image overlap might not be used in the first scan, thus constituting a further difference between the first and second sets of conditions which might otherwise be identical.

In some embodiments, the termination condition of the first set of conditions is such that the first survey terminates after analytical data has been collected from the full region of interest, and wherein the dwell time, magnification and resolution are the same for the first set of conditions as for the second set of conditions.

Typically, the entire method is automated. That is, a survey algorithm may be used to implement the first and second surveys with the applied first and second condition sets, such that no user intervention is required. The method may also be performed such that each of the first and second surveys is automated, and the method further comprises a decision step performed after the first survey and before the second survey, wherein the outcome of the decision step is used in the selecting of the parts used for data collection in the second survey and the deciding of the order in which they are used. In such embodiments, the decision step may optionally be automated, again to reduce or remove the need for user intervention at this stage. Alternatively, the decision step may comprise an action performed by a user. For example, in some embodiments it would be desired to pause the method between the first and second surveys so as to allow a user to review the analytical data collected in the first survey prior to the second survey being performed, or so as to include a decision process, which may potentially be preconfigured with its own settings and so be automated, that makes a decision as to whether or not to perform a full second survey and apply an optimised order, based upon the requirements of a user.

In some embodiments, the decision step is automated, and in some embodiments the decision step may comprise an action performed by a user. This action may comprise a confirmation that a second survey is to be performed based upon an inspection of the data collected from the first survey, or it may comprise an input of parameters or conditions to be applied to the second survey.

Typically, the method is for automated analysis of a specimen in a microscope. In other words, the survey scan would typically be performed in a fully automated manner wherein the full run of the second survey is initiated upon completion of the first survey.

In accordance with the invention there is also provided an apparatus for analysis of a specimen in a microscope, the apparatus comprising programmable controls for stage positioning,
the apparatus being configured to record and process data collected from a region of interest on the specimen surface, wherein the apparatus is configured to perform analysis comprising:

a first survey that collects analytical data from the region of interest on the specimen surface using a first set of conditions a second survey that collects additional analytical data from selected parts of the region of interest on the specimen surface using a second set of conditions, different from the first set of conditions, wherein the analytical data from the first survey is used to select the parts used for data collection in the second survey and to decide the order in which they are used.

The first set of conditions and data collected during the first survey may be chosen so as to give faster coverage of an area on the specimen than for the second set of conditions. The apparatus typically includes a microscope comprising a first detector for collecting the analytical data. The apparatus typically includes a microscope comprising a second detector for collecting the additional analytical data.

The apparatus may comprise a device for directing a particle beam upon the specimen as well as programmable controls for particle beam positioning.

One or both of the first and second detectors may be configured to detect x-rays or electrons emitted from the specimen resulting from the particle beam being directed upon the specimen, so as to collect the data. Alternatively, or in addition, one or both of the first and second detectors comprises an optical image sensor configured to collect optical image data representing the specimen.

One or both of the first and second detectors may comprise an electron detector or an x-ray detector, and the data representing a region of interest on the specimen surface comprises electron signal data and/or x-ray signal data.

As discussed above, the analysis may typically comprise moving the specimen with respect to a detector so as to sequentially bring sub-regions or parts of the specimen into the field of view of the detector collecting analytical data or additional analytical data. The apparatus may thus comprise a moveable stage for supporting the specimen, configured to position the selected parts of the region of interest on the specimen surface within the field of view of a detector for collecting additional analytical data in the decided order, during the second survey.

Figure 1:
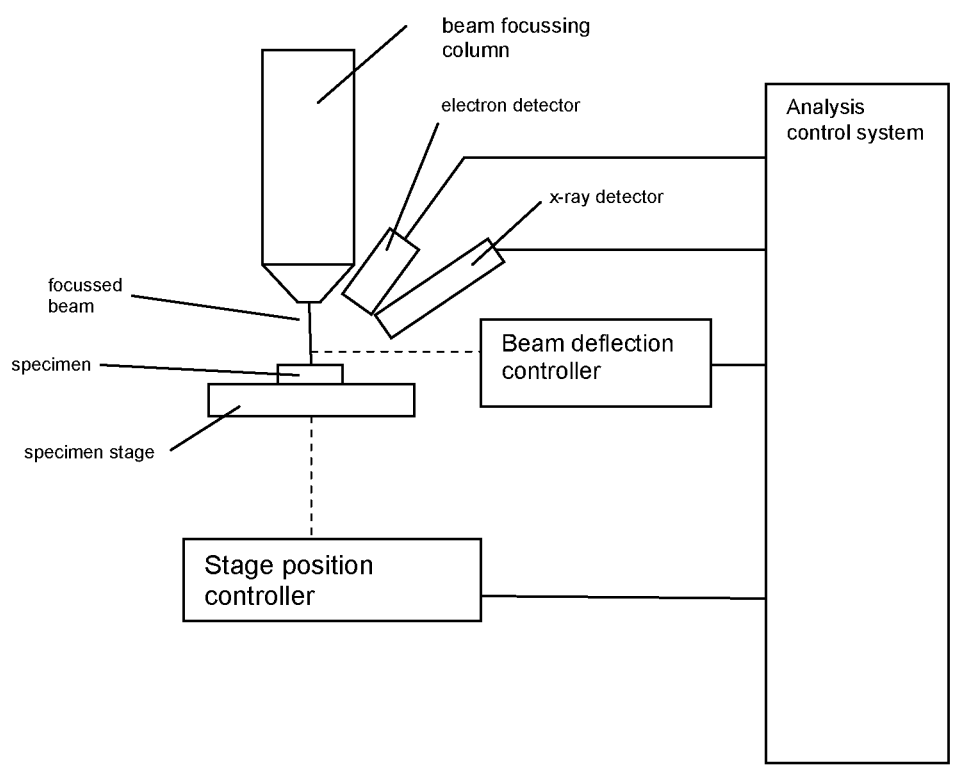
FIG. 1 shows schematically components required for automated particle analysis.
Figure 2:
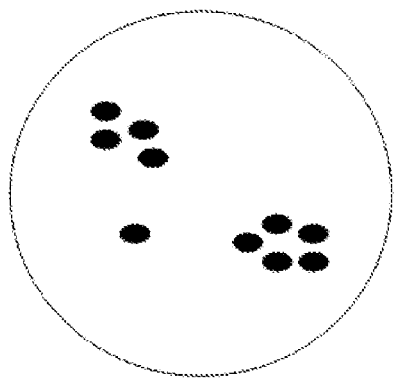
FIG. 2 shows schematically a conventional approach for particle analysis in a scanning electron microscope.
Figure 2:
Figure 2:
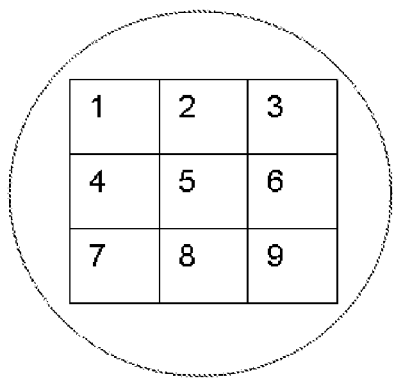
Figure 2:
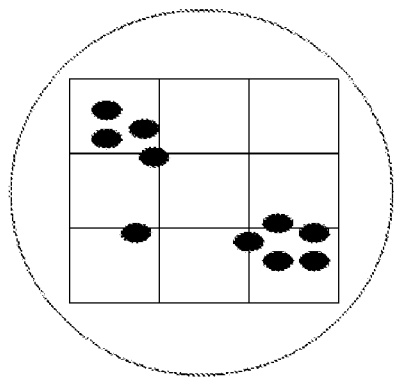
Figure 2:
Figure 2:
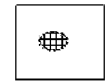

In one embodiment, all fields are first scanned at the target resolution to obtain electron signal data only ("preliminary survey"). The shape and number of particles for each field is determined to find the total number of particles of interest. X-ray data would normally be collected from every particle of interest. However, if the requirement is to acquire x ray data for only a certain percentage of all particles of interest present on the surface, then with knowledge of the total number of particles present, it is possible to stop collecting x-ray data when a certain percentage has been analysed thus saving time collecting unnecessary x-ray data. Preferably, if fields containing a higher number of particles are visited first, the number of stage movements can be minimised. For example, in FIG. 2(d) positioning the stage to acquire x-ray data for particles in fields 9 and 1 would give enough data to cover a high percentage of all particles present on the specimen without moving the stage back to any other position.

Figure 3:
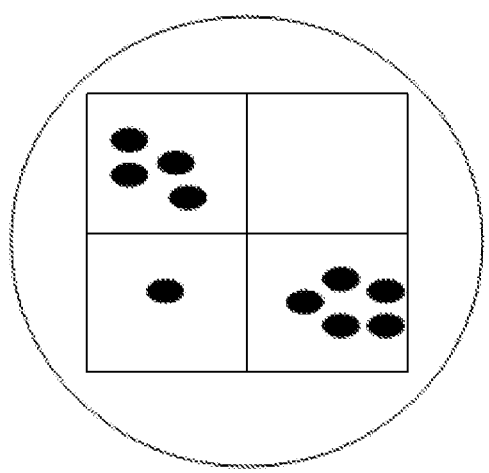
FIG. 3 shows a specimen area covered by larger contiguous fields of view in accordance with the present invention.

In a second embodiment, the preliminary survey conditions are chosen to cover the specimen area much faster than would normally be required to collect target data and this inevitably involves some loss of accuracy. For example, if the electron beam grid covers a larger area on the specimen, there may be more geometric distortion and the grid resolution may be coarser but it will then require fewer stage movements to cover points all over the specimen. FIG. 3 shows the same specimen as for FIG. 2, but larger fields are scanned using bigger electron beam deflection so that only 4 stage movements are needed for contiguous fields to cover the whole area. Because electron deflection is much faster than mechanical stage movement, electron images covering the whole specimen area can be obtained much faster than when 9 stage movements are needed as for FIG. 2(d).

If the electron beam grid is coarser for the preliminary survey, then the accuracy of feature dimensions will be less and some very small features may be missed altogether. Furthermore, if the electron beam dwell per point is reduced, the noise on the signal will increase and the accuracy of the scan positioning may be less. However, although these techniques to reduce the time for the preliminary scan make the accuracy worse than required for the target data, it is still possible to collect a statistical overview of particle number and morphology that is adequate to optimise the strategy for the target data collection. By changing the conditions it is thus possible to collect some data over the whole specimen in a small fraction of the time that it would take to record electron signal data under the conditions required to collect target data of required accuracy. The data obtained from the preliminary survey of the specimen is now used to optimise the strategy for the target data collection. If there are no particles of interest in a particular area then time can be saved by not collecting target data of required accuracy for any fields of view in this area (e.g. field 3 in FIG. 2). If there are no particles of interest anywhere on the specimen, then there is no need to spend any time collecting target data of the required accuracy on this specimen. If the aim is to collect representative data from many particles of particular size or shape, then the preliminary survey can show where target data should be collected that will give the highest number of suitable particles without wasting time scanning regions with a very low count of suitable particles. Even if x-ray data is not being collected, a fast preliminary scan over the whole specimen with possibly compromised accuracy for measurement of particle morphology, can still be beneficial. Statistical data from the preliminary scan can determine the best ordering of fields for collecting data at the target resolution and the target data acquisition can be stopped as soon as a high enough percentage of particles have been accurately measured.

Figure 4:
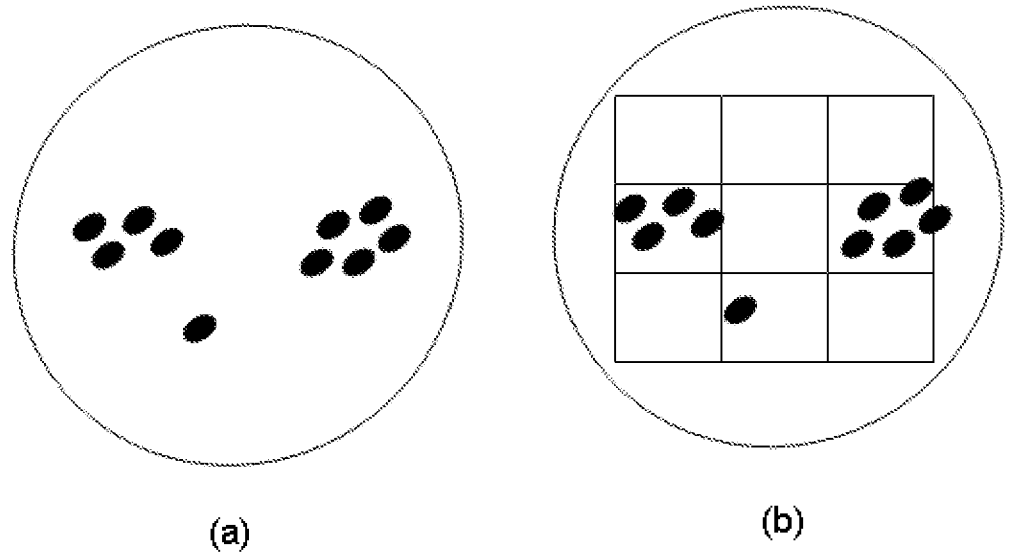
FIG. 4 shows the specimen of FIG. 2 rotated before mounting on a stage.

In cleanliness applications, after testing a sample on a first electron beam instrument it may be necessary to confirm the result from the same sample using a second instrument in a different location. When the sample is transferred to the second instrument, it may not be possible to reproduce the orientation and relative positioning of the sample. FIG. 4 shows an example where the sample of FIG. 2 has suffered an unexpected rotation before being mounted on the stage. If the regular target data acquisition sequence was used, the fields 1 and 2 would not contain any particles of interest. However, if a preliminary survey is used to determine the spatial density of particles of interest and the target data acquisition is then organised to move the stage to fields in inverse order of particle density on both instruments (e.g. fields 9,1 in FIGS. 2 and 6,4 in FIG. 4) not only will the required surveys be completed faster, but also similar regions, ordered by particle density, will be assayed on both instruments, even if the orientation and positioning of the sample is uncertain. Thus, both the efficiency and consistency of the cleanliness evaluation will be improved.

Thus, although it is known that a specimen survey in a scanning electron microscope can be optimised to minimise the time required to collect morphological and analytical data of required accuracy, our invention can improve productivity by utilising the results of an additional preliminary survey to alter the strategy for obtaining target data of the required accuracy.

Although the invention has been described with reference to an incident electron beam, imaging with electron signals and x-ray analysis, the same principles would apply for an focussed incident ion beam which also produces electron signals and any analytical signal stimulated by an incident beam such as from cathodoluminescence, Auger or low-loss backscattered electrons instead of x-rays. The claims below are intended to claim these alternatives also. The invention could apply to any instrument that can acquire image data fast over a restricted field of view and needs specimen stage movement to move the specimen so that a large area can be studied. In a system where an optical image is acquired with a microscope that has a limited field of view and stage movements are needed to bring new parts of the specimen surface into the field of view, a fast preliminary scan using a low magnification, large field of view, for each optical image can be used to detect and measure particles and use the results to optimise the strategy for collecting data at higher magnification at different stage positions. If a fast imaging method with limited field of view is able to detect particles but analytical data is required that requires a longer acquisition time to collect the same field of view, then a preliminary scan can be used to optimise the strategy for collecting the slower analytical data at each field of view. If an optical image using all wavelengths could be obtained rapidly whereas a filtered optical image that gave additional analytical information from the same field of view was much slower, a preliminary scan could be used to optimise data collection for analytical information on particles.

The invention claimed is:

1. A method for analysis of a specimen in a microscope, the method comprising:
   performing a first survey that collects analytical data from a region of interest on the specimen surface using a first set of conditions;
   performing a second survey that collects additional analytical data from selected parts of the region of interest on the specimen surface using a second set of conditions, different from the first set of conditions;
   wherein the analytical data from the first survey is used to select the parts used for data collection in the second survey and to decide the order in which they are used,
   wherein using the analytical data from the first survey comprises:
   identifying features of interest on the specimen from the analytical data, and
   generating an optimal order in which the additional analytical data is collected from each of the selected parts, such that additional analytical data is collected from a part containing a greater proportion of the features of interest before additional analytical data is collected from a part containing a smaller proportion of the features of interest.

2. A method according to claim 1, wherein the analytical information data from the first survey is used to decide the position within the region of interest and order for the selected parts used for data collection in the second survey.

3. A method according to claim 1, wherein the first set of conditions and data collected during the first survey are chosen so as to give faster coverage of an area on the specimen than for the second set of conditions.

4. A method according to claim 1, wherein the conditions of the first and second sets of conditions comprise any of: magnification, image resolution, image dwell time, a grey level threshold, energy-dispersive x-ray spectroscopy settings, and a survey termination condition.

5. A method according to claim 1, wherein the first survey comprises collecting the analytical data from the region of interest by moving the specimen with respect to a first detector of the microscope for collecting the analytical data such that each of a plurality of sub-regions is sequentially brought into the field of view of the first detector for a given dwell time.

6. A method according to claim 1, wherein the second survey comprises collecting the additional analytical data from each of the selected parts by moving the specimen with respect to a second detector of the microscope for collecting additional analytical data such that each of the selected parts is sequentially brought into the field of view of the second detector for a given dwell time.

7. A method according to claim 6, wherein the dwell time is sufficiently long to collect the additional analytical data with a predetermined resolution or signal-to-noise ratio.

8. A method according to claim 1, wherein the collection of additional analytical data in the second survey comprises collecting energy-dispersive x-ray spectroscopy data.

9. A method according to claim 1, wherein using the analytical data from the first survey further comprises selecting the parts used for data collection in the second survey such that the selected parts contain a predetermined fraction of the features of interest.

10. A method according to claim 1, wherein the features of interest are particles or other discrete regions present on a surface of the specimen.

11. A method according to claim 1, wherein each of the first and second surveys comprises directing a particle beam upon the specimen and detecting the resulting x-rays or electrons emitted from the specimen so as to collect the data.

12. A method according to claim 1, wherein the using the analytical data from the first survey comprises identifying features of interest on the specimen from the analytical data, and wherein each of the first and second sets of conditions includes a termination condition in accordance with which each respective survey is terminated, and wherein the termination condition of the second set of conditions is decided such that the second survey is terminated upon additional analytical data having been collected from a predetermined fraction of the features of interest.

13. A method according to claim 12, wherein the termination condition of the first set of conditions is such that the first survey terminates after analytical data has been collected from the full region of interest, and wherein the dwell time, magnification and resolution are the same for the first set of conditions as for the second set of conditions.

14. An apparatus for analysis of a specimen in a microscope, the apparatus comprising programmable controls for stage positioning,
the apparatus being configured to record and process data collected from a region of interest on the specimen surface,
wherein the apparatus is configured to perform analysis comprising:
a first survey that collects analytical data from the region of interest on the specimen surface using a first set of conditions
a second survey that collects additional analytical data from selected parts of the region of interest on the specimen surface using a second set of conditions, different from the first set of conditions,
wherein the analytical data from the first survey is used to select the parts used for data collection in the second survey and to decide the order in which they are used,
wherein using the analytical data from the first survey comprises:
identifying features of interest on the specimen from the analytical data, and
generating an optimal order in which the additional analytical data is collected from each of the selected parts, such that additional analytical data is collected from a part containing a greater proportion of the features of interest before additional analytical data is collected from a part containing a smaller proportion of the features of interest.

15. An apparatus according to claim 14, wherein the first set of conditions and data collected during the first survey are chosen so as to give faster coverage of an area on the specimen than for the second set of conditions.

16. An apparatus according to claim 14, wherein the apparatus includes a microscope comprising a first detector for collecting the analytical data.

17. An apparatus according to claim 16, wherein the apparatus includes a microscope comprising a second detector for collecting the additional analytical data.

18. An apparatus according to claim 14, wherein the apparatus comprises a device for directing a particle beam upon the specimen and programmable controls for particle beam positioning.

19. An apparatus according to claim 17, wherein one or both of the first and second detectors is configured to detect x-rays or electrons emitted from the specimen resulting from the particle beam being directed upon the specimen, so as to collect the data.

20. An apparatus according to claim 17, wherein one or both of the first and second detectors comprises an optical image sensor configured to collect optical image data representing the specimen.

* * * * *